US009532755B2

(12) United States Patent
Choi et al.

(10) Patent No.: US 9,532,755 B2
(45) Date of Patent: Jan. 3, 2017

(54) X-RAY COMPUTED TOMOGRAPHIC IMAGING APPARATUS AND METHOD FOR SAME

(75) Inventors: Sung Il Choi, Gyeonggi-do (KR); Hyo Sung Cho, Gyeonggi-do (KR)

(73) Assignee: VATECH Co., Ltd., Gyeonggi-do (KR)

( * ) Notice: Subject to any disclaimer, the term of this patent is extended or adjusted under 35 U.S.C. 154(b) by 593 days.

(21) Appl. No.: 13/521,926

(22) PCT Filed: Jan. 13, 2011

(86) PCT No.: PCT/KR2011/000267
§ 371 (c)(1), (2), (4) Date: Jul. 12, 2012

(87) PCT Pub. No.: WO2011/087306
PCT Pub. Date: Jul. 21, 2011

(65) Prior Publication Data
US 2012/0307960 A1    Dec. 6, 2012

(30) Foreign Application Priority Data

Jan. 13, 2010    (KR) .................. 10-2010-0003220

(51) Int. Cl.
*A61B 6/03*    (2006.01)
*A61B 6/14*    (2006.01)
*A61B 6/00*    (2006.01)

(52) U.S. Cl.
CPC .............. *A61B 6/14* (2013.01); *A61B 6/032* (2013.01); *A61B 6/4452* (2013.01); *A61B 6/545* (2013.01); *A61B 6/582* (2013.01); *A61B 6/588* (2013.01)

(58) Field of Classification Search
CPC ........... A61B 6/03; A61B 6/032; A61B 6/545; G01N 23/046
(Continued)

(56) References Cited

U.S. PATENT DOCUMENTS 5,452,337 A     9/1995  Endo et al.
6,692,441 B1 *  2/2004  Poland ................... G06T 15/08
                                                          128/916
(Continued)

FOREIGN PATENT DOCUMENTS

JP    2003-116837 A    4/2003
JP    2003-175031 A    6/2003
(Continued)

OTHER PUBLICATIONS

M D Lee et al., "CT reconstruction algorithm for a dental panoramic X-ray unit", Physics in Medicine and Biology, Dec. 1, 1992, pp. 2161-2174, vol. 37, No. 12, Institute of Physics Publishing, Bristol GB.
(Continued)

*Primary Examiner* — Jack Berman
*Assistant Examiner* — Kevin Chung
(74) *Attorney, Agent, or Firm* — IP Legal Services, LLC (57) ABSTRACT

Disclosed are an X-ray computed tomographic imaging apparatus and a method for same. The X-ray computed tomographic imaging apparatus of the present invention comprises: a tomograph which radiates light onto an object being imaged by tomography, and detects the light passing through the object being imaged by tomography; a magnification rate determining unit which determines the magnification rate of an image of the object being imaged by tomography using the hardware property of the tomograph and/or the size of an input voxel; and a magnification rate controller which moves the tomography in accordance with the determined magnification rate, thereby obtaining images having a high resolution.

16 Claims, 6 Drawing Sheets (58) Field of Classification Search
USPC .............................................................. 378/4
See application file for complete search history.

(56) References Cited

U.S. PATENT DOCUMENTS

| | | | |
|---|---|---|---|
| 7,347,622 | B2 | 3/2008 | Sadakane et al. |
| 2003/0179851 | A1 | 9/2003 | Ishikawa |
| 2004/0151277 | A1 | 8/2004 | Ohara |
| 2007/0127794 | A1* | 6/2007 | Niogi ................... G06K 9/3233 382/128 |
| 2007/0269000 | A1* | 11/2007 | Partain ................... A61B 6/032 378/37 |
| 2008/0095299 | A1* | 4/2008 | Kohler et al. ..................... 378/4 |
| 2008/0118024 | A1* | 5/2008 | Cho et al. ....................... 378/13 |
| 2008/0165920 | A1* | 7/2008 | De Man et al. ................ 378/17 |
| 2009/0046835 | A1 | 2/2009 | Kodama et al. |
| 2010/0246755 | A1* | 9/2010 | Suzuki et al. .................. 378/11 |

FOREIGN PATENT DOCUMENTS

| | | | | |
|---|---|---|---|---|
| JP | 2007-170921 A | 7/2007 | | |
| JP | 2008-148866 A | 7/2008 | | |
| JP | WO 2009063974 A1 * | 5/2009 | ............. | A61B 6/032 |
| KR | 20-0261705 Y1 | 1/2002 | | |
| KR | 10-2009-0130719 A | 12/2009 | | |
| WO | WO 2009063974 A1 * | 5/2009 | ............... | A61B 6/03 |

OTHER PUBLICATIONS

European Patent Office, European Search Report of European Patent Application No. 11733093.6, Jul. 19, 2013.

* cited by examiner

X-RAY COMPUTED TOMOGRAPHIC IMAGING APPARATUS AND METHOD FOR SAME

CROSS REFERENCE TO RELATED APPLICATIONS

This application is a National Stage Patent Application of PCT International Patent Application No PCT KR2011/000267 (filed on Jan. 13, 2011) under 35 U.S.C. §371, which claims priority to Korean Patent Application No. 10-2010-0003220 (filed on Jan. 13, 2010), the teachings of which are incorporated herein in their entireties by reference.

TECHNICAL FIELD

The present invention relates, in general, to an X-ray Computed Tomography (CT) imaging apparatus and method and, more particularly, to an X-ray CT imaging apparatus and method that image an object at an optimum magnification ratio.

BACKGROUND ART

Generally, an X-ray CT imaging apparatus includes an X-ray tube that radiates X-rays onto an object, a detector that detects X-rays having been transmitted through the object, a rotating mechanism unit that rotates with the X-ray tube and the detector mounted thereon, and a computer device that reconstructs data obtained by the detector into image information.

Such a typical X-ray CT imaging apparatus having the above configuration captures tomograms of the object while the rotating mechanism unit rotates around the object. The CT imaging of the object is performed at regular fine angles, and pieces of X-ray projection data obtained when imaging is performed at regular fine angles are reconstructed into sectional image information about the object using mathematical operations such as an iterative reconstruction technique, a back-projection reconstruction technique, or a filtered back-projection reconstruction technique.

In particular, dental CT is a device for obtaining transmitted information while an X-ray tube and an X-ray detector, which are respectively aligned on the left and right sides of an object, rotate in parallel with a ground surface so as to professionally diagnose only specific regions such as the head, neck, jaw and teeth of a patient in dental and oral clinics.

In the case where a specific region of a patient is imaged using dental CT, if images are captured at a fixed magnification ratio regardless of the region to be imaged, the quality of the reconstructed images of the CT may be deteriorated.

DISCLOSURE

Technical Problem

An object of the present invention is to provide an X-ray CT imaging apparatus and method that obtain images at an optimum magnification ratio depending on a Field Of View (FOV) and the size of a voxel.

Technical Solution

The present invention provides an X-ray Computed Tomography (CT) imaging apparatus, including an imaging device for radiating light (e.g., X-ray) onto an object and detecting light (e.g., X-ray) having been transmitted through the object; a magnification ratio determination unit for determining a magnification ratio for images of the object using at least one of hardware attributes of the imaging device and a size of an input voxel; and a magnification ratio controller for moving the imaging device in accordance with the determined magnification ratio.

The magnification ratio determination unit may include a first magnification ratio determination unit for determining a first magnification ratio based on the hardware attributes of the imaging device; a second magnification ratio determination unit for determining a second magnification ratio based on the size of the voxel; and a third magnification ratio determination unit for determining a value between the first magnification ratio and the second magnification ratio to be the magnification ratio for the images of the object.

The hardware attributes may include at least one of a focal spot size, a pixel size, and resolution of the imaging device.

The imaging device may include a light source for radiating the light (e.g., X-ray) onto the object; and a detector for detecting the light (e.g., X-ray) having been transmitted through the object.

The magnification ratio controller may control movement of at least one of the light source and the detector in accordance with the determined magnification ratio.

The images of the object may be reconstructed into a three-dimensional (3D) image using adaptive filtered panoramic back projection.

The adaptive filtered panoramic back projection may be configured to reconstruct the images by back-projecting the images obtained by the imaging device around a virtual shaft that is a shaft based on light-receiving surfaces of a detector in the imaging device, applying different filter values depending on a distance between the virtual shaft and the detector, and then correcting the images.

The imaging device may be any one of an imaging device for dentistry, an imaging device for a head and a neck, and an imaging device for otorhinolaryngology.

The present invention provides a Computed Tomography (CT) imaging method, including determining a magnification ratio for images of an object using at least one of hardware attributes of an imaging device, which radiates light (e.g., X-ray) onto the object and detects light (e.g., X-ray) having been transmitted through the object, and a size of an input voxel; moving the imaging device in accordance with the determined magnification ratio; and obtaining images of the object while rotating the moved imaging device.

The determining the magnification ratio may include determining a first magnification ratio based on the hardware attributes of the imaging device; determining a second magnification ratio based on the size of the voxel; and determining a value between the first magnification ratio and the second magnification ratio to be the magnification ratio for the images of the object.

The hardware attributes may include at least one of a focal spot size, a pixel size, and resolution of the imaging device.

The imaging device may include a light source for radiating the light (e.g., X-ray) onto the object; and a detector for detecting the light (e.g., X-ray) having been transmitted through the object.

The moving the imaging device may be configured to move at least one of the light source and the detector in accordance with the determined magnification ratio.

The CT imaging method may further include, after the obtaining the images, reconstructing the images of the object into a three-dimensional (3D) image using adaptive filtered panoramic back projection.

The adaptive filtered panoramic back projection may be configured to reconstruct the images by back-projecting the images obtained by the imaging device around a virtual shaft that is a shaft based on light-receiving surfaces of a detector in the imaging device, applying different filter values depending on a distance between the virtual shaft and the detector, and then correcting the images.

The imaging device may be any one of an imaging device for dentistry, an imaging device for a head and a neck, and an imaging device for otorhinolaryngology.

Advantageous Effects

According to the present invention, since an object is imaged at an optimum magnification ratio, there is an advantage in that resolution becomes higher, the Signal to Noise Ratio (SNR) increases, and aliasing artifact decreases, compared to existing images.

There is an advantage in that when a virtual shaft is changed, the filter value of a variable filter is also adaptively changed, thus obtaining higher-resolution images.

Further, images can be obtained at an optimum magnification ratio depending on the regions to be imaged.

BEST MODE

An X-ray Computed Tomography (CT) imaging apparatus according to an embodiment of the present invention includes an imaging device for radiating light (e.g., X-ray) onto an object and detecting light (e.g., X-ray) having been transmitted through the object; a magnification ratio determination unit for determining a magnification ratio for images of the object using at least one of hardware attributes of the imaging device and a size of an input voxel; and a magnification ratio controller for moving the imaging device in accordance with the determined magnification ratio.

A CT imaging method according to an embodiment of the present invention includes determining a magnification ratio for images of an object using at least one of hardware attributes of an imaging device, which radiates light (e.g., X-ray) onto the object and detects light (e.g., X-ray) having been transmitted through the object, and a size of an input voxel; moving the imaging device in accordance with the determined magnification ratio; and obtaining images of the object while rotating the moved imaging device.

MODE FOR INVENTION

Hereinafter, the present invention will be described in detail with reference to the attached drawings.

The attached drawings illustrating preferred embodiments of the present invention and the contents describing the attached drawings should be referred to so as to gain a sufficient understanding of the present invention, advantages in the operations of the present invention, and the objects that are achieved by the implementation of the present invention.

Figure 1:
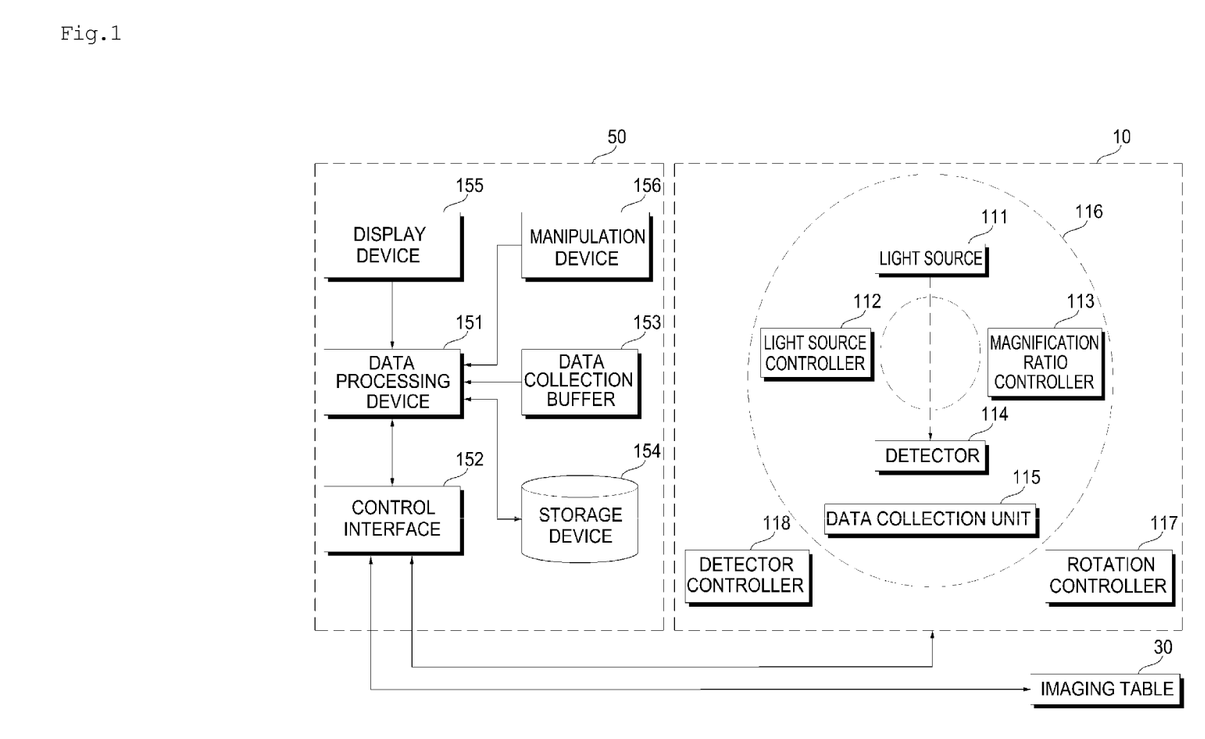
FIG. 1 is a block diagram showing an X-ray CT imaging apparatus according to an embodiment of the present invention.

FIG. 1 is a block diagram showing an X-ray CT imaging apparatus according to an embodiment of the present invention.

As shown in FIG. 1, the X-ray CT imaging apparatus includes a scan gantry 10, an imaging table 30, and a manipulation console 50.

The scan gantry includes a light source 111 that radiates light (here, light may preferably be an X ray) under the control of a light control unit, a detector 114 that detects light (e.g., X-ray) having been transmitted through an object, a data collection unit 115 that collects signals detected by individual detection elements in the detector 114 (hereinafter referred to as "detected signals") and converts the signals into digital data, and a rotating element 116 that rotates with the above components mounted thereon under the control of a rotation control unit. Mutual connections between the light source 111 and a light source controller 112 and between the rotating element 116 and the rotation controller 117 are omitted from the drawing.

The imaging table 30 is configured to transfer the object (not shown) to the inside and the outside of a light radiation space in the scan gantry 10.

The manipulation console 50 includes a data collection buffer 153 for temporarily storing the digital data provided by the data collection unit 115, a data processing device 151 for reconstructing a three-dimensional (3D) image using pieces of digital data for a plurality of views collected by the data collection buffer 153, a display device 155 for displaying the 3D image, a control interface 152 for functioning as an interface when the data processing device 151 controls the rotating element 116 and components mounted on the rotating element 116 (the light source 111, the detector 114, etc.), and a manipulation device 156 composed of the manipulation buttons of a user or the like.

In detail, the light source 111, the light source controller 112, the detector 114, and the data collection unit 115 are mounted on the rotating element 116 and are rotated under the control of the rotation control unit. That is, while the rotating element 116 having the individual components mounted thereon is rotating around the object at regular intervals of a fine angle, pieces of transmitted information (tomographic image information), that is, the detected signals, are continuously obtained at respective locations.

The light source 111 generates predetermined light (e.g., X-ray) and radiates the light (e.g., X-ray) onto the object under the control of the light source controller 112. The radiated light (e.g., X-ray) is transmitted through the object, and is then transferred to the detector 114.

The signals detected by the individual detection elements in the detector 114, that is, pieces of digital data, are collected by the data collection unit 115.

The light source 111 and the detector 114 may be regarded as an imaging device because they image the object. This imaging device may preferably be any one of an imaging device for dentistry, an imaging device for a head and a neck, and an imaging device for otorhinolaryngology. Further, the scan gantry includes a magnification ratio controller 113 for adjusting a magnification ratio by moving the above-described imaging device.

The data collection unit 115 converts a series of voltage signals generated according to the amount of light detected by the detector 114 into digital data. The digital data, that is, the tomographic image information, is transferred to the data collection buffer 153. Then, the data collection buffer 153 sequentially transmits pieces of incoming digital data to the data processing device 151.

The data processing device 151 determines an optimum magnification ratio so that the object is imaged at the optimum magnification ratio, transmits the optimum magnification ratio to the magnification ratio controller 113 via the control interface 152, and obtains a reconstructed 3D image by applying an image reconstruction algorithm to the object transmitted information (tomographic information), that is, the digital data, transmitted from the data collection buffer 153.

In particular, a user sets the Field Of View (FOV) of an object desired to be imaged and the size of a voxel using the manipulation device 156. The data processing device 151 determines a magnification ratio suitable for the set FOV and the set size of the voxel, and this operation will be described in detail below.

Figure 2:
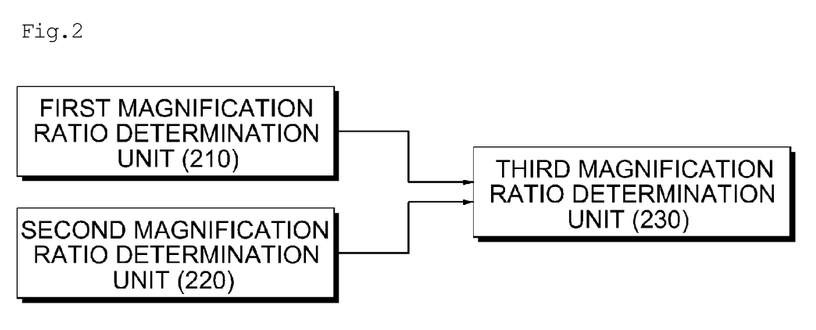
FIG. 2 is a block diagram showing the magnification ratio determination unit of a data processing device for determining an optimum magnification ratio for images according to an embodiment of the present invention.

FIG. 2 is a block diagram showing the magnification ratio determination unit of the data processing device for determining an optimum magnification ratio for images according to an embodiment of the present invention.

As shown in FIG. 2, the data processing device 151 includes a first magnification ratio determination unit 210 for determining a first magnification ratio based on hardware attributes of the imaging device, a second magnification ratio determination unit 220 for determining a second magnification ratio based on the size of a voxel, and a third magnification ratio determination unit 230 for determining an optimum magnification ratio for images based on the first and second magnification ratios. Here, the hardware attributes may include at least one of the focal spot size of the light source 111, the pixel size of the detector 114, and the resolution of the detector 114. Hereinafter, for the sake of convenience of description, it is assumed that the hardware attributes denote all of the focal spot size, the pixel size, and the resolution of the detector 114.

Figure 3:
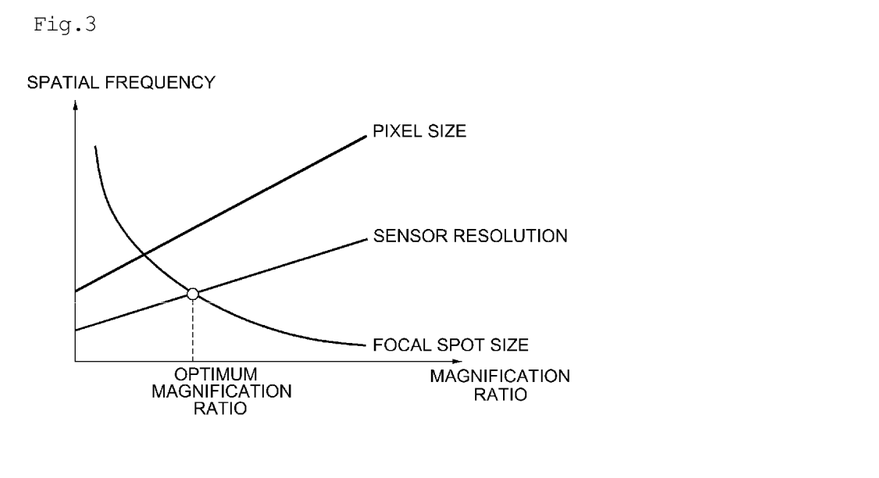
FIG. 3 is a reference diagram showing the operation of a first magnification ratio determination unit according to an embodiment of the present invention.

FIG. 3 is a reference diagram showing the operation of the first magnification ratio determination unit according to an embodiment of the present invention.

The imaging device can magnify and image the object. When it is assumed that the magnification ratio at this time is on a horizontal axis and the spatial frequency of images that are to be obtained by the imaging device is on a vertical axis, relationships among each of the focal spot size, the pixel size, and the sensor resolution, the magnification ratio, and the spatial frequency, and can be depicted, as shown in FIG. 3.

The focal spot size f, the magnification ratio M, and the spatial frequency u are represented by the following Equation 1:

$$u_{focalspot} = \frac{M}{(M-1)f} \qquad \text{Equation 1}$$

where $u_{focalspot}$ denotes a spatial frequency appearing when only the focal spot size and the magnification ratio are taken into consideration.

Meanwhile, the pixel size d, the magnification ratio M, and the spatial frequency u can be represented by the following Equation 2:

$$u_{nyquist} = \frac{M}{2d} \qquad \text{Equation 2}$$

where $u_{nyquist}$ denotes a spatial frequency appearing when only the pixel size and the magnification ratio are taken into consideration.

Meanwhile, the detector resolution, that is, the sensor resolution b, the magnification ratio M, and the spatial frequency u can be represented by the following Equation 3:

$$u_{solution} = \frac{M}{b} \qquad \text{Equation 3}$$

where $u_{solution}$ denotes a spatial frequency appearing when only the detector resolution and the magnification ratio are taken into consideration.

The first magnification ratio determination unit 210 is aware of curves and straight lines shown in FIG. 3. In other words, the first magnification ratio determination unit 210 previously stores information about relationships between spatial frequencies and magnification ratios corresponding to each of the pixel size, sensor resolution, and focal spot size. The first magnification ratio determination unit 210 determines the minimum value of spatial frequencies corresponding to the pixel size, sensor resolution, and focal spot size for each magnification ratio. The determined minimum value is on the curve MF indicated by a dotted line in FIG. 3. The first magnification ratio determination unit 210 determines the magnification ratio M at the maximum spatial frequency of the determined minimum values, that is, spatial frequencies on the curve MF, to be a first magnification ratio.

The second magnification ratio determination unit 220 determines a second magnification ratio Pm based on the size of the voxel by using the following Equation 4:

$$P_m = \frac{2d}{E_v} \qquad \text{Equation 4}$$

where d denotes the size of a pixel and Ev denotes the size of a voxel.

The third magnification ratio determination unit 230 determines a value between the first magnification ratio and the second magnification ratio to be an optimum third magnification ratio. Preferably, the third magnification ratio may be the mean of the first magnification ratio and the second magnification ratio. Further, the third magnification ratio determination unit 230 determines the optimum third magnification ratio depending on FOV, the size and type of the detector 114, etc. and, in this case, may determine the optimum third magnification ratio based on the reference data. The reference data may be optimum third magnification ratios previously obtained from experiments depending on FOV, the size of the detector 114, the type of detector 114, etc.

The magnification ratio controller 113 controls the imaging device depending on the magnification ratio determined by the third magnification ratio determination unit 230. In detail, the magnification ratio is (distance between the light source 111 and the detector 114)/(distance between the light source 111 and the object). Therefore, the magnification ratio controller 113 moves the imaging device so that the determined magnification ratio is satisfied.

Figure 4:
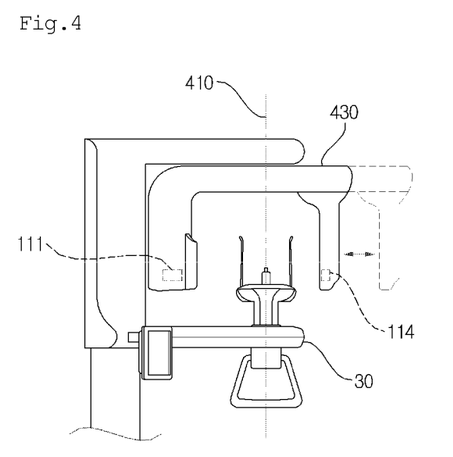
FIG. 4 is a sectional diagram showing an X-ray CT imaging apparatus having a movable detector according to an embodiment of the present invention.

FIG. 4 is a sectional diagram showing an X-ray CT imaging apparatus having a movable detector according to an embodiment of the present invention. As shown in FIG. 4, an element 430 to which the detector 114 is attached around the shaft 410 of the rotating element 116 can be moved in a horizontal direction. Then, the magnification ratio controller 113 laterally moves the detector 114, so that the determined magnification ratio is satisfied.

Figure 5:
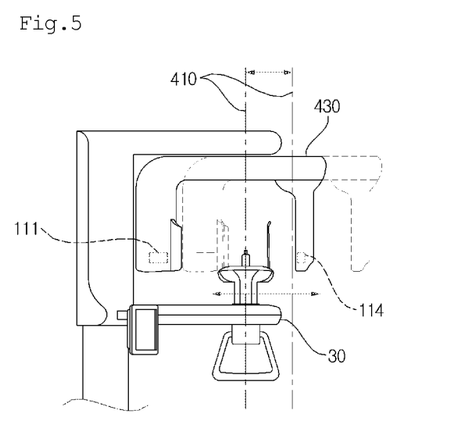
FIG. 5 is a sectional diagram showing an X-ray CT imaging apparatus having a movable imaging device according to an embodiment of the present invention.

FIG. 5 is a sectional diagram showing an X-ray CT imaging apparatus having a movable imaging device according to an embodiment of the present invention. As shown in FIG. 5, an element to which the imaging device is attached can be moved in a horizontal direction. Then, the imaging device is moved laterally under the control of the magnification ratio controller, so that the determined magnification ratio is satisfied.

In this way, since the optimum magnification ratio is determined depending on the FOV and the size of the voxel, and the object is imaged at the determined magnification ratio, there is an advantage in that the resolution becomes higher, the Signal to Noise Ratio (SNR) increases, and aliasing artifact decreases, compared to existing images.

Further, the image reconstruction unit (not shown) of the data processing device 151 obtains a reconstructed 3D image by applying an image reconstruction algorithm to object transmitted information (tomographic information), that is, digital data, transmitted from the data collection buffer 153.

In this case, the image reconstruction unit may reconstruct the digital data into a 3D image using adaptive filtered panoramic back projection. That is, each obtained image is back-projected around a virtual shaft, and filter values based on the distance R between the virtual shaft and the detector 114 are calculated and applied. Here, the virtual shaft denotes a shaft based on the light-receiving surfaces of the detector 114, on which light is detected, and the distance R between the virtual shaft and the detector 114 is always changed, so that different filter values must be applied.

Figure 6:
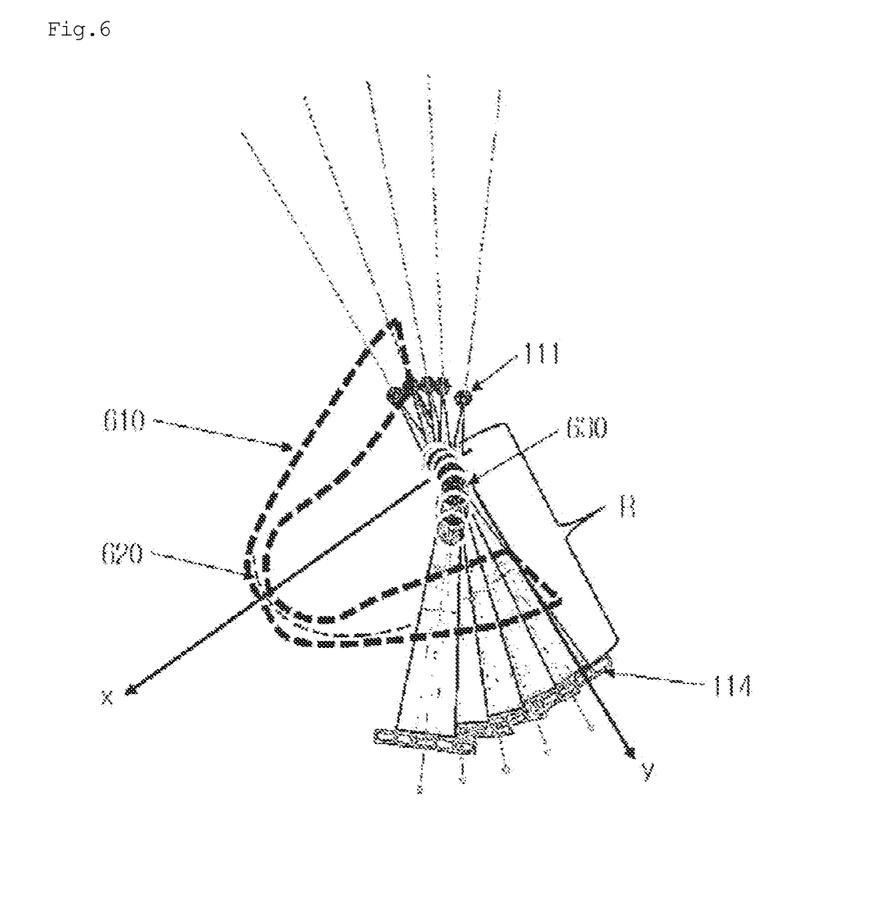
FIGS. 6 and 7 are diagrams showing a virtual shaft according to an embodiment of the present invention.
Figure 7:
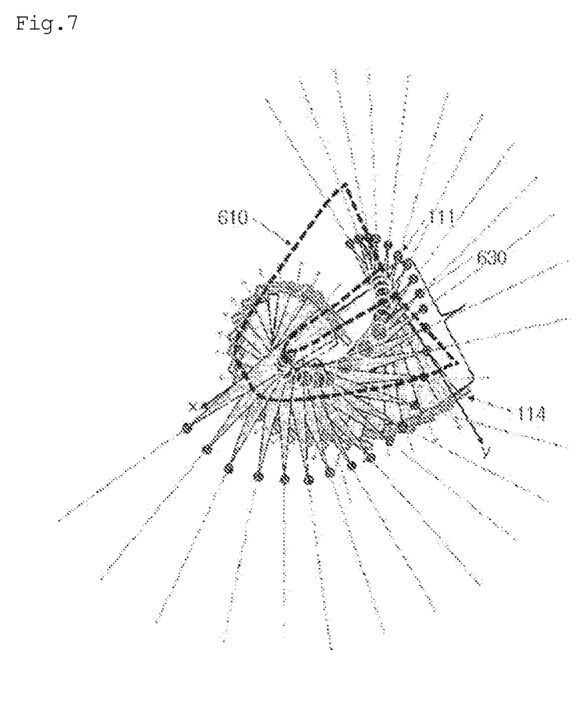

FIGS. 6 and 7 are diagrams showing a virtual shaft according to an embodiment of the present invention. As shown in FIGS. 6 and 7, an object is disposed between a light source 111 for radiating light (e.g., X-ray) onto an image layer located in a region of interest in the object and a detector 114 for detecting light (e.g., X-ray) having been transmitted through the image layer.

Further, an X-ray is radiated onto the start point of the image layer, so that an image starts to be obtained in a portion of the start point of the image layer. Next, in order to continuously image subsequent portions of the image layer, the light source 111 and the detector 114 are moved along a first track while the virtual shaft is moved along a second track differing from the first track. In this case, the light source 111 and the detector 114 continuously radiate and detect light even while being moved. Further, the distance R between the virtual shaft and the light-receiving surface of the detector 114 is continuously varied.

Next, the light source 111 and the detector 114 are moved up to a portion of the end point of the image layer, so that images are obtained.

That is, the present invention can obtain images while moving the light source 111 and the detector 114 along a new track obtained by merging a track based on panoramic imaging with a track based on CT imaging. In this way, there is the advantage of obtaining a 3D image having the shape of a music bow even while simplifying an imaging track and shortening the imaging time. Further, the data processing device 151 at this time reconstructs the images into a 3D image using adaptive filtered panoramic back projection.

The basic principal of adaptive filtered panoramic back projection is similar to that of typical back projection which reconstructs images while filling a 3D shape with frame images in a radiation direction up to the focal position of the light source 111 and filling the 3D shape with all the frames in an overlapping manner.

However, the adaptive filtered panoramic back projection denotes a reconstruction scheme in which when the virtual shaft is continuously moved along with the movement of the imaging device (the light source 111 and the detector 114), a back projection rotating position is adjusted depending on the position of the shaft of the rotating element 116, and individual filter values corresponding to a distance R between the virtual shaft and the detector 114 are calculated and then used to correct images because the distance R is variable rather than constant upon designing a filter for eliminating blurring and artifact. Further, the above filter, the filter value of which is changed as the distance R between the virtual shaft and the detector 114 is not constant and is variable, is referred to as a variable filter.

Figure 8:
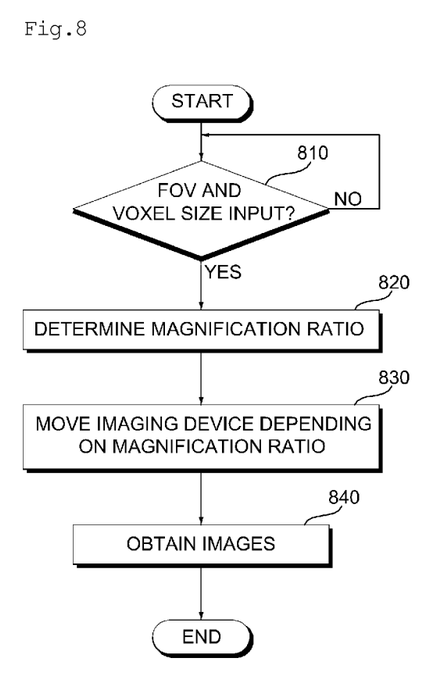
FIG. 8 is a flowchart showing a method of capturing images depending on a magnification ratio according to an embodiment of the present invention.

FIG. 8 is a flowchart showing a method of capturing images depending on magnification ratios according to an embodiment of the present invention.

As shown in FIG. 8, when a user inputs FOV and the size of a voxel via the manipulation unit (S810-Y), the magnification ratio determination unit determines a magnification ratio depending on the FOV and the size of the voxel (S820).

In detail, the first magnification ratio determination unit 210 determines a first magnification ratio in consideration of the hardware attributes of the imaging device (for example, a focal spot size, a pixel size, and sensor resolution). The second magnification ratio determination unit 220 determines a second magnification ratio based on the size of the voxel. Thereafter, the third magnification ratio determination unit 230 determines a final magnification ratio based on the first magnification ratio and the second magnification ratio.

The determined magnification ratio is transmitted to the magnification ratio controller 113 via the control interface 152, and the magnification ratio controller 113 moves the imaging device so that the imaging device images the object at the magnification ratio (S830). When the imaging device is moved, only the detector 114 can be moved in a horizontal direction with the light source 111 fixed or, alternatively, both the light source 111 and the detector 114 can be moved.

The imaging device images the object at the determined magnification ratio a plurality of times, and then obtains a plurality of images (S840). That is, when the rotating element 116 rotates at regular intervals of a fine angle around the object, the detector 114 detects transmitted information about light of the light source 111 (tomographic image information) having been transmitted through the object at respective positions, and applies the transmitted information to the data collection unit 115. The data collection unit 115 converts a series of voltage signals generated depending on the transmission information about light of the light source 111 (tomographic image information) into digital data, and transfers the digital data to the data collection buffer 153. The data collection buffer 153 sequentially transmits digital data about incoming tomographic images to the data processing device 151. The data processing device 151 obtains a reconstructed 3D image by applying an image reconstruction algorithm to the object transmitted information (tomographic information).

A program for executing the high-resolution panoramic image obtainment method according to at least one of the above-described embodiments of the present invention on a computer can be stored in a computer-readable recording medium. In this case, examples of the computer-readable recording medium include a magnetic storage medium (e.g., Read Only Memory (ROM), a floppy disc, a hard disc, etc.) and an optical readable medium (e.g., Compact Disk-ROM (CD-ROM), a Digital Versatile Disc (DVD), etc.).

Although the preferred embodiments of the present invention have been illustrated and described, the present invention is not limited by the above specific embodiments, and various modifications are possible by those skilled in the art, without departing from the scope and spirit of the invention as disclosed in the accompanying claims. These modifications should be understood separately from the technical spirit or prospect of the present invention.

INDUSTRIAL APPLICABILITY

There is an advantage in that when a specific region of a patient is imaged using dental CT, the object is imaged at an optimum magnification ratio, so that resolution becomes higher, the Signal to Noise Ratio (SNR) increases, and aliasing artifact decreases compared to existing images. Further, there is an advantage in that when a virtual shaft is changed, filter values of a variable filter are adaptively changed, thus obtaining higher-resolution images.

The invention claimed is:

1. An X-ray Computed Tomography (CT) imaging apparatus, comprising:
   an imaging device for radiating an X-ray onto an object and detecting the X-ray having been transmitted through the object;
   a magnification ratio determination unit for determining a magnification ratio for images of the object using at least one of hardware attributes of the imaging device and a size of an input voxel; and
   a magnification ratio controller for moving the imaging device in accordance with the determined magnification ratio,
   wherein the hardware attributes comprise at least one of a focal spot size, a pixel size, and resolution of the imaging device; and
   wherein the magnification ratio determination unit includes:
      a first magnification ratio determination unit for determining a first magnification ratio based on the hardware attributes of the imaging device;
      a second magnification ratio determination unit for determining a second magnification ratio based on the size of the input voxel; and
      a third magnification ratio determination unit for determining a third magnification ratio for the images of the object, based on the first magnification ratio and the second magnification ratio, wherein the determined third magnification ratio for the images of the object is greater than a less value of the first and second magnification ratios and is less than a greater value of the first and second magnification ratios.

2. The X-ray CT imaging apparatus according to claim 1, wherein the imaging device comprises: an X-ray source for radiating the X-ray onto the object; and a detector for detecting the X-ray having been transmitted through the object.

3. The X-ray CT imaging apparatus according to claim 2, wherein the magnification ratio controller controls movement of at least one of the X-ray source and the detector in accordance with the determined third magnification ratio.

4. The X-ray CT imaging apparatus according to claim 1, wherein the images of the object are reconstructed into a three-dimensional (3D) image using adaptive filtered panoramic back projection.

5. The X-ray CT imaging apparatus according to claim 4, wherein the adaptive filtered panoramic back projection is configured to reconstruct the images by back-projecting the images obtained by the imaging device around a virtual shaft that is a shaft based on X-ray-receiving surfaces of a detector in the imaging device, applying different filter values depending on a distance between the virtual shaft and the detector, and then correcting the images.

6. The X-ray CT imaging apparatus according to claim 1, wherein the imaging device is any one of an imaging device for dentistry, an imaging device for a head and a neck, and an imaging device for otorhinolaryngology.

7. A Computed Tomography (CT) imaging method, comprising:
   determining a magnification ratio for images of an object using at least one of hardware attributes of an imaging device, which radiates an X-ray onto the object and detects the X-ray having been transmitted through the object, and a size of an input voxel;
   moving the imaging device in accordance with the determined magnification ratio; and
   obtaining images of the object while rotating the moved imaging device,
   wherein the hardware attributes comprise at least one of a focal spot size, a pixel size, and resolution of the imaging device; and
   wherein the determining the magnification ratio comprises:
      determining a first magnification ratio based on the hardware attributes of the imaging device;
      determining a second magnification ratio based on the size of the input voxel; and
      determining a third magnification ratio for the images of the object, based on the first magnification ratio and the second magnification ratio, wherein the determined third magnification ratio for the images of the object is greater than a less value of the first and second magnification ratios and is less than a greater value of the first and second magnification ratios.

8. The CT imaging method according to claim 7, wherein the imaging device comprises: an X-ray source for radiating the X-ray onto the object; and a detector for detecting the X-ray having been transmitted through the object.

9. The CT imaging method according to claim 8, wherein the moving the imaging device includes:
   moving at least one of the X-ray source and the detector in accordance with the determined third magnification ratio.

10. The CT imaging method according to claim 7, further comprising, after the obtaining the images, reconstructing the images of the object into a three-dimensional (3D) image using adaptive filtered panoramic back projection.

11. The CT imaging method according to claim 10, wherein the adaptive filtered panoramic back projection is configured to reconstruct the images by back-projecting the images obtained by the imaging device around a virtual shaft that is a shaft based on X-ray-receiving surfaces of a detector in the imaging device, applying different filter values depending on a distance between the virtual shaft and the detector, and then correcting the images.

12. The CT imaging method according to claim 7, wherein the imaging device is any one of an imaging device for dentistry, an imaging device for a head and a neck, and an imaging device for otorhinolaryngology.

13. The X-ray CT imaging apparatus according to claim 1, wherein the determined third magnification ratio for the images of the object is a mean value of the first magnification ratio and the second magnification ratio.

14. The CT imaging method according to claim 7, wherein the determined third magnification ratio for the images of the object is a mean value of the first magnification ratio and the second magnification ratio.

15. The X-ray CT imaging apparatus according to claim 1, wherein the third magnification ratio for the images of the object is determined using predetermined reference data.

16. The CT imaging method according to claim 7, wherein the third magnification ratio for the images of the object is determined using predetermined reference data.

\* \* \* \* \*